United States Patent
Hecht et al.

(10) Patent No.: US 7,786,064 B1
(45) Date of Patent: Aug. 31, 2010

(54) IONIC LIQUIDS DERIVED FROM FUNCTIONALIZED ANIONIC SURFACTANTS

(75) Inventors: Stacie Ellen Hecht, West Chester, OH (US); Scott Leroy Cron, Fairfield, OH (US); Jeffrey John Scheibel, Loveland, OH (US); Gregory Scot Miracle, Hamilton, OH (US); Kenneth Richard Seddon, Donahadee (GB); Martyn Earle, Belfast (GB); Harambage Quintus Nimal Gunaratne, Belfast (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/771,588

(22) Filed: Apr. 30, 2010

Related U.S. Application Data

(62) Division of application No. 11/263,382, filed on Oct. 31, 2005, now Pat. No. 7,737,102.

(60) Provisional application No. 60/624,125, filed on Nov. 1, 2004.

(51) Int. Cl.
*C11D 1/22* (2006.01)
*C11D 1/14* (2006.01)
*C11D 1/29* (2006.01)
*C11D 1/75* (2006.01)

(52) U.S. Cl. .................. 510/237; 510/238; 510/341; 510/350; 510/351; 510/357; 510/423; 510/424; 510/427; 510/492; 510/503

(58) Field of Classification Search ............... 510/237, 510/238, 341, 350, 351, 357, 423, 424, 427, 510/492, 503
See application file for complete search history.

(56) References Cited

U.S. PATENT DOCUMENTS

| | | | |
|---|---|---|---|
| 3,282,728 | A | 11/1966 | Lacroux et al. |
| 4,126,573 | A | 11/1978 | Johnston et al. |
| 4,189,311 | A | 2/1980 | Laqua et al. |
| 4,717,507 | A | 1/1988 | Schwadtke et al. |
| 4,756,850 | A | 7/1988 | Nayar |
| 5,705,466 | A | 1/1998 | Baillely |
| 5,731,101 | A | 3/1998 | Sherif et al. |
| 5,798,329 | A | 8/1998 | Taylor et al. |
| 5,827,602 | A | 10/1998 | Koch et al. |
| 6,048,388 | A | 4/2000 | Schwarz et al. |
| 6,086,785 | A | 7/2000 | Roesler et al. |
| 6,277,808 | B1 | 8/2001 | Tcheou et al. |
| 6,288,281 | B1 | 9/2001 | Nemeth et al. |
| 6,339,182 | B1 | 1/2002 | Munson et al. |
| 6,372,829 | B1 | 4/2002 | Lamanna et al. |
| 6,479,446 | B1 | 11/2002 | Sherry et al. |
| 6,521,584 | B1 | 2/2003 | Soldanski |
| 6,521,585 | B1 | 2/2003 | Yamashita et al. |
| 6,767,882 | B1 | 7/2004 | Jagannath et al. |
| 6,808,557 | B2 | 10/2004 | Holbrey et al. |
| 6,824,599 | B2 | 11/2004 | Swatloski |
| 6,900,313 | B2 | 5/2005 | Wasserscheid et al. |
| 2001/0014654 | A1 | 8/2001 | Davister et al. |
| 2004/0005286 | A1 | 1/2004 | Giroud |
| 2004/0007693 | A1 | 1/2004 | Moulton et al. |
| 2004/0035293 | A1 | 2/2004 | Davis, Jr. |
| 2004/0054231 | A1 | 3/2004 | Abbott et al. |
| 2004/0077519 | A1 | 4/2004 | Price et al. |
| 2004/0096932 | A1 | 5/2004 | Kragl et al. |
| 2004/0097755 | A1 | 5/2004 | Abbott et al. |
| 2004/0133058 | A1 | 7/2004 | Arlt et al. |
| 2004/0198902 | A1 | 10/2004 | Yui et al. |
| 2006/0090777 | A1 | 5/2006 | Hecht et al. |
| 2006/0094615 | A1 | 5/2006 | Hecht et al. |
| 2006/0094616 | A1 | 5/2006 | Hecht et al. |
| 2006/0094617 | A1 | 5/2006 | Price et al. |
| 2006/0094620 | A1 | 5/2006 | Jordan, IV et al. |
| 2006/0094621 | A1 | 5/2006 | Jordan, IV |
| 2006/0189499 | A1 | 8/2006 | Hecht et al. |

FOREIGN PATENT DOCUMENTS

| | | |
|---|---|---|
| CN | 1081629 | 3/2002 |
| DE | 101 37 047 A1 | 2/2003 |
| EP | 0 723 006 A | 7/1996 |

(Continued)

OTHER PUBLICATIONS

John S. Wilks, Air and Water Stable 1-Ethyl-3-methylimidazolium Based Ionic Liquids, The rank J. Seller Research Laboratory, United States Air Force Academy, Colorado, US, 1992, pp. 965-967.

(Continued)

*Primary Examiner*—Gregory R Del Cotto
(74) *Attorney, Agent, or Firm*—Andrew J. Mueller; Leonard W. Lewis

(57) ABSTRACT

A novel class of ionic liquids and methods for their preparation are disclosed. Specifically, these novel ionic liquids can be derived from anionic surfactants, such as alkyl aryl sulfonates, and mid-chain branched derivatives of alkyl sulfates, alkyl alkoxy sulfates, and alkyl aryl sulfonates. In addition, novel ionic liquids can be derived from other anionic surfactants, such as methyl ester sulfonates (MES), alkyl glycerol ether sulfonates, and alpha olefin sulfonates. Anions may be paired with a variety of cations to achieve various advantageous properties. The present invention also relates to compositions containing these novel ionic liquids and method of using the same.

6 Claims, No Drawings

FOREIGN PATENT DOCUMENTS

| | | | |
|---|---|---|---|
| EP | 1 454 978 A | 9/2004 |
| FR | 1296756 | 5/1962 |
| FR | 2 101 710 A | 3/1972 |
| GB | 1 014 539 A | 12/1965 |
| JP | 3064368 | 3/1991 |
| JP | 5178798 | 7/1993 |
| JP | 06009767 A2 | 1/1994 |
| JP | 10265674 | 6/1998 |
| JP | 11084603 A2 | 3/1999 |
| JP | 2915208 B2 | 7/1999 |
| WO | WO98/32822 | * | 7/1998 |
| WO | WO 98/55581 A | 12/1998 |
| WO | WO 00/01793 A | 1/2000 |
| WO | WO 01/19200 A1 | 3/2001 |
| WO | WO 01/77486 A1 | 10/2001 |
| WO | WO 02/34722 A1 | 5/2002 |
| WO | WO 02/38784 | 5/2002 |
| WO | WO 03/074494 A1 | 9/2003 |
| WO | WO 2004/022670 A1 | 3/2004 |
| WO | WO 2004/035018 A2 | 4/2004 |
| WO | WO 2004/067739 A2 | 8/2004 |

OTHER PUBLICATIONS

J D Holbrey, Clean Products and Processes (1999) pp. 223, 236.
Richard Swatloski, Dissolution of Cellose with Ionic Liquids, Center for Green Manufacturing and Department of Chemistry, the University of Alabama, (2002) pp. 4974-4975.
David Bradley, Super Solvents, Technology Ireland, Sep. 1999, pp. 47 & 48.
Brycki, Szafran, Formation of the Homoconjugated Cation (N—0 H O—N)+ of $N$-Dodecyl-$N$, $N$-Dimethylamine Oxide in Carbon Tetrachloride, Journal of Molecular Structure, 239 (1190) pp. 1-11.
Golding, J, Methanesulfonate and $p$-toluenesulfonate salts of the $N$-methyl-$N$-alkylpyrrolidinium and quaternary ammonium cations: novel low cost ionic liquids, Centre for Green Chemistry, School of Chemistry, Monash University, pp. 223-229, Apr. 2002.
International Search Report, mailed Jun. 30, 2006.
XP 002375958, Anufrieva, V., Chem. Abstract.
XP 002375959, Beilstein Institut zur Forderung, Chem. Abstract.
XP 002375960, J. Amer. Chem, Chem. Abstract.
XP 002375961, Beilstein Institut zur Forderung, Chem. Abstract.
XP 002375962, Beilstein Institut zur Forderung, Chem. Abstract.
XP 002375963, Beilstein Institut zur Forderung, Chem. Abstract.

* cited by examiner

IONIC LIQUIDS DERIVED FROM FUNCTIONALIZED ANIONIC SURFACTANTS

CROSS REFERENCE TO RELATED APPLICATIONS

This application is a Divisional of U.S. application Ser. No. 11/263,382, filed Oct. 31, 2005, now U.S. Pat. No. 7,737,102, which claims priority under 35 U.S.C. §119(e) to U.S. Provisional Application Ser. No. 60/624,125, filed Nov. 1, 2004.

FIELD OF THE INVENTION

The present invention relates to a novel class of ionic liquids and methods for their preparation. Specifically, these novel ionic liquids can be derived from anionic surfactants, such as alkyl aryl sulfonates, and mid-chain branched derivatives of alkyl sulfates, alkyl alkoxy sulfates, and alkyl aryl sulfonates. In addition, novel ionic liquids can be derived from other anionic surfactants, such as methyl ester sulfonates (MES), alkyl glycerol ether sulfonates, and alpha olefin sulfonates. Anions may be paired with a variety of cations to achieve various advantageous properties. The present invention also relates to compositions containing these novel ionic liquids and methods of using the same.

BACKGROUND OF THE INVENTION

Generally speaking, ionic liquids refer to a specific class of molten salts which are liquid at temperatures of 100° C. or below. Ionic liquids have very low vapor pressure and generate virtually no hazardous vapors. Due to the charged species comprising the ionic fluids, they provide a highly polar medium.

In recent years, there is much interest in this class of novel materials. Ionic liquids have been extensively evaluated as environmental-friendly or "green" alternatives to conventional organic solvents for a broad range of organic synthetic applications. In addition, ionic liquids have also been used in organic synthesis applications as catalysts. Conventional ionic liquids for a wide range of chemical processes are described in "*Ionic Liquid*" by J. D. Holbrey and K. R. Seddon, and in *Clean Products and Processes*, Vol. 1, pp. 223-236 (1999). Other examples of ionic liquids are described in U.S. patents: U.S. Pat. No. 6,048,388; U.S. Pat. No. 5,827,602; U.S. patent Publications: US 2003/915735A1; US 2004/0007693A1; US 2004/0035293A1; and PCT publications: WO 02/26701; WO 03/074494; WO 03/022812; WO 04/016570.

Furthermore, ionic liquids have also been found useful in chemical separation and extraction, as described, for example, in WO 02/074718.

Ionic liquids also have applications in electrochemistry, for example, in fuel cells, electrodeposition processes and other electrochemical applications.

Additionally, ionic liquids have been shown to be effective in applications where water-based chemistry can be problematic (for example, applications involving proton transfer or nucleophilicity), or in applications where certain coordination chemistry could have a damaging effect on the substrates involved.

Moreover, ionic liquids have found applications in consumer product formulations and industrial product formulations for surface treating, air treating, cleaning and other benefits, as described in US 2004/0077519A1.

It is desirable to develop new classes of ionic liquids by converting certain conventional solid or semi-solid actives used in consumer or industrial product formulations into ionic liquids. Thus, the ionic liquids can be used as replacements of the traditional actives, such as surfactants, and are easier to incorporate into the formulations. Moreover, new classes of ionic liquids can be derived from selective pairings between functional actives (for example, surfactant derived anions can be paired with softener derived cations) such that the resulting ionic liquids can have multiple active functionalities to provide multiple benefits that previously require multiple actives in the formulation to achieve.

It is also desirable to develop new classes of ionic liquids with advantageous properties. For example, the ionic nature and/or fluidity of these novel ionic liquids provide additional advantages, such as improved soil removal capability, lower viscosity of the formulation, higher concentration of the active functionalities can be incorporated.

SUMMARY OF THE INVENTION

The present invention relates to an ionic compound comprising a cation and an anion selected from the group consisting of:

(1) alkyl aryl sulfonates;

(2) mid-chain branched alkyl sulfates, alkyl aryl sulfonates, and alkyl polyoxyalkylene sulfates;

(3) methyl ester sulfonates;

(4) alkyl glycerol ether sulfonates containing C8-C22 alkyl groups;

(5) alpha olefin sulfonates, paraffin sulfonates; and (6) mixtures thereof.

The present invention also relates to a composition comprising the above ionic compounds, and method of using the same to treat hard and soft surfaces.

DETAILED DESCRIPTION OF THE INVENTION

"Consumer product" as used herein refers to a material that is used by a user (i.e., a consumer) in, on or around their person, house (such as kitchen surfaces, bathroom surfaces, carpets, floors, windows, minors and countertops), car (such as automobile interiors, automobile exteriors, metal surfaces and windshields), and other personal or household articles (such as dishware, fabrics, cookware, utensils, tableware and glassware). "Consumer product composition" may also include the material used by institutional users (such as hotels, restaurants, offices) or by service providers (such as commercial dry cleaners and janitorial services).

"Industrial product" as used herein refers to a material that is used in a commercial process of making an article. Non-limiting examples include degreasing compositions for degreasing articles, such as metals; and textile treating compositions for processing and/or finishing textiles into fabric articles, such as garments, draperies.

"Treating" as used herein refers to a composition or a process for cleaning, refreshing or maintaining the target surface or air. For example, "refreshing" includes the processes of removing the wrinkled or worn appearance from a fabric article, or imparting a pleasant odor to a fabric article, air, or a hard surface.

"Surface", "target surface" or "treated surface" as used herein refers to an inanimate, non-biological surface. Non-limiting examples of such surfaces are found in soft surfaces such as fabrics, fabric articles, textiles, fibers; and hard surfaces such as dishware, cookware, utensils, glassware, countertops, kitchen surfaces, bathroom surfaces, floors, windows, car interior and exterior, metal, and combinations thereof.

"Derived from" as used herein refers to ionic compounds of interest may be mixed or made from original materials such that the ionic compounds may be present in simple mixtures of the original materials, or mixtures of the original materials and the reaction or decomposition products thereof, or mixtures of reaction or decomposition products.

"Hydrophilic ionic compound" or "water miscible ionic compound" as used herein refers to ionic compound that is partially or wholly miscible with water, i.e. it is capable of forming a visually homogenous or transparent mixture with water according to the Water Miscibility Test described herein.

"Hydrophobic ionic compounds" or "water immiscible ionic compounds" as used herein refers to ionic compounds that are relatively immiscible with water.

The present invention relates to novel ionic liquids that are derived from compounds that have been used as surfactants in detergent formulations for laundry, dish washing and hard surface cleaning. By reacting or mixing various surfactants commonly used in detergent formulations with properly chosen counterions, these surfactants can be converted into ionic compounds having different characteristics.

For example, the surfactant-derived ionic compounds are hydrophobic or water immiscible. In other examples, the surfactant-derived ionic compounds are water miscible.

In some embodiments, the surfactant derived ionic compounds are liquids at temperatures of about 100° C. or below. That is, these ionic compounds exhibit a first order transition or a melting point of about 100° C. or below, as measured by Differential Scanning Calorimetry (DSC). In other embodiments, the surfactant derived ionic compounds do not exhibit a melting point but are "flowable" at a temperature of about 100° C. or below. As used herein, the term "flowable" means the ionic compound exhibits a viscosity of less than about 10,000 cps at a temperature of about 100° C., preferably at a temperature range from about 20° C. to about 80° C. and more preferably from about 20° C. to about 60° C. Due to these differences in the ionic compounds, the term "ionic liquid" as used herein is meant to include all ionic compounds exhibiting one or more of the above characteristics. For certain applications, it is desirable to have ionic compounds that are liquids or "flowable" at temperatures ranging from about 20 to about 80° C., i.e., the typical fabric or dish washing temperatures.

It should be understood that the terms "ionic liquid", "ionic compound", and "IL" encompass ionic liquids, ionic liquid composites, and mixtures (or cocktails) of ionic liquids. The ionic liquid can comprise an anionic IL component and a cationic IL component. When the ionic liquid is in its liquid form, these components may freely associate with one another (i.e., in a scramble). As used herein, the term "cocktail of ionic liquids" refers to a mixture of two or more, preferably at least three, different and charged IL components, wherein at least one IL component is cationic and at least one IL component is anionic. Thus, the pairing of three cationic and anionic IL components in a cocktail would result in at least two different ionic liquids. The cocktails of ionic liquids may be prepared either by mixing individual ionic liquids having different IL components, or by preparing them via combinatorial chemistry. Such combinations and their preparation is discussed in further detail in US 2004/0077519A1 and US 2004/0097755A1. As used herein, the term "ionic liquid composite" refers to a mixture of a salt (which can be solid at room temperature) with a proton donor Z (which can be a liquid or a solid) as described in the references immediately above. Upon mixing, these components turn into a liquid at about 100° C. or less, and the mixture behaves like an ionic liquid.

Surfactant-Derived Ionic Liquids

Nonlimiting examples of surfactant-derived ionic liquids of the present invention comprise anions such as:

(1) Alkyl aryl sulfonates, nonlimiting examples include tosylate, alkyl aryl sulfonates having linear or branched, saturated or unsaturated $C_8$-$C_{14}$ alkyls; alkyl benzene sulfonates (LAS) such as $C_{11}$-$C_{18}$ alkyl benzene sulfonates; sulfonates of benzene, cumene, toluene, xylene, t-butylbenzene, di-isopropylbenzene, or isopropylbenzene; naphthalene sulfonates and $C_{6-14}$ alkyl naphthalene sulfonates, such as Petro® (from Akzo Nobel Surface Chemistry); sulfonates of petroleum, such as Monalube 605® (from Uniqema);

(2) mid-chain branched alkyl sulfates (HSAS), mid-chain branched alkyl aryl sulfonates (MLAS) and mid-chain branched alkyl polyoxyalkylenesulfates; nonlimiting examples of MLAS are disclosed in U.S. Pat. No. 6,596,680; U.S. Pat. No. 6,593,285; and U.S. Pat. No. 6,020,303;

(3) methyl ester sulfonates (MES);

(4) alkyl glycerol ether sulfonates having 8 to 22 carbon atoms in the alkyl moiety;

(5) alpha olefin sulfonates (AOS) and paraffin sulfonates, nonlimiting examples include $C_{10\text{-}22}$ alpha-olefin sulfonates, available as Bio Terge AS-40® from Stepan Company; and (6) mixtures thereof.

The surfactant-derived anions described above can be paired with one or more of the following cations:

(a) Cations (i.e., in the protonated, cationic form) of amine oxides, phosphine oxides, or sulfoxides: nonlimiting examples include amine oxide cations containing one $C_{8-18}$ alkyl moiety and 2 moieties selected from the group consisting of $C_{1-3}$ alkyl groups and $C_{1-3}$ hydroxyalkyl groups; phosphine oxide cations containing one $C_{10-18}$ alkyl moiety and 2 moieties selected from the group consisting of $C_{1-3}$ alkyl groups and $C_{1-3}$ hydroxyalkyl groups; and sulfoxide cations containing one $C_{10-18}$ alkyl moiety and a moiety selected from the group consisting of $C_{1-3}$ alkyl and $C_{1-3}$ hydroxyalkyl moieties; in some embodiments, the amine oxide cations have the following formula:

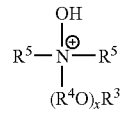

wherein $R^3$ is an $C_{8-22}$ alkyl, $C_{8-22}$ hydroxyalkyl, $C_{8-22}$ alkyl phenyl group, and mixtures thereof; $R^4$ is an $C_{2-3}$ alkylene or $C_{2-3}$ hydroxyalkylene group or mixtures thereof; x is from 0 to about 3; and each $R^5$ is independently an $C_{1-3}$ alkyl or $C_{1-3}$ hydroxyalkyl group or a polyethylene oxide group containing an average of from about 1 to about 3 ethylene oxide groups; the $R^5$ groups may be attached to each other, e.g., through an oxygen or nitrogen atom, to form a ring structure; other exemplary amine oxide cations include $C_{10}$-$C_{18}$, $C_{10}$, $C_{10}$-$C_{12}$, and $C_{12}$-$C_{14}$ alkyl dimethyl amine oxide cations, and $C_8$-$C_{12}$ alkoxy ethyl dihydroxy ethyl amine oxide cations;

(b) Betaines having the general formula:

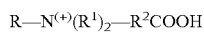

wherein R is selected from the group consisting of alkyl groups containing from about 10 to about 22 carbon atoms, preferably from about 12 to about 18 carbon atoms, alkyl aryl and aryl alkyl groups containing a similar number of carbon atoms with a benzene ring treated as equivalent to about 2 carbon atoms, and similar structures interrupted by amido or ether linkages; each $R^1$ is an alkyl group containing from 1 to about 3 carbon atoms; and $R^2$ is an alkylene group containing from 1 to about 6 carbon atoms; nonlimiting examples of betaines include dodecyl dimethyl betaine, acetyl dimethyl betaine, dodecyl amidopropyl dimethyl betaine, tetradecyl dimethyl betaine, tetradecyl amidopropyl dimethyl betaine, dodecyl dimethyl ammonium hexanoate; and amidoalkylbetaines which are disclosed in U.S. Pat. Nos. 3,950,417; 4,137,191; and 4,375,421; and British Patent GB No. 2,103,236; in another embodiment, the cation may be a sulfobetaine, which are disclosed in U.S. Pat. No. 4,687,602;

(c) Diester quaternary ammonium (DEQA) cations of the type:

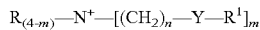

wherein each R substituent is selected from hydrogen; $C_1$-$C_6$ alkyl or hydroxyalkyl, preferably methyl, ethyl, propyl, or hydroxyethyl, and more preferably methyl; poly($C_1$-$C_3$ alkoxy), preferably polyethoxy; benzyl; or a mixture thereof; m is 2 or 3; each n is from 1 to about 4; each Y is —O—(O)C—, —C(O)—O—, —NR—C(O)—, or —C(O)—NR—; with the proviso that when Y is —O—(O)C— or —NR—C(O)—, the sum of carbons in each $R^1$ plus one is $C_{12}$-$C_{22}$, preferably $C_{14}$-$C_{20}$, with each $R^1$ being a hydrocarbyl, or substituted hydrocarbyl group; in one embodiment, the DEQA cation is an alkyl dimethyl hydroxyethyl quaternary ammonium as discussed in U.S. Pat. No. 6,004,922; in another embodiment, the DEQA cation has the general formula:

$$R_3N^+CH_2CH(YR^1)(CH_2YR^1)$$

wherein each Y, R, $R^1$ have the same meanings as before; in yet another embodiment, the DEQA cation is $[CH_3]_3N^{(+)}[CH_2CH(CH_2O(O)CR^1)O(O)CR^1]$ wherein each $R^1$ is in the range of $C_{15}$ to $C_{19}$;

(d) Alkylene quaternary ammonium cations having the formula:

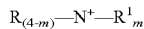

wherein each m is 2 or 3; each R is independently an alkyl or hydroxyalkyl $C_1$-$C_6$ moiety, preferably methyl, ethyl, propyl or hydroxyethyl, and more preferably methyl; each $R^1$ is independently a linear or branched, saturated or unsaturated $C_6$-$C_{22}$ alkyl or alkoxy moiety, preferably $C_{14}$-$C_{20}$ moiety, but no more than one $R^1$ being less than about $C_{12}$ and then the other $R^1$ is at least about $C_{16}$; or hydrocarbyl or substituted hydrocarbyl moiety, preferably $C_{10}$-$C_{20}$ alkyl or alkenyl, most preferably $C_{12}$-$C_{18}$ alkyl or alkenyl; in one embodiment, the cation is dialkylenedimethyl ammonium, such as dioleyldimethyl ammonium available from Witco Corporation under the tradename Adogen® 472; in another embodiment, the cation monoalkenyltrimethyl ammonium, such as monooleyltrimethyl ammonium, monocanolatrimethyl ammonium, and soyatrimethyl ammonium;

(e) Difatty amido quaternary ammonium cations such as:

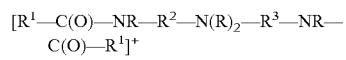

wherein R and $R^1$ are as defined in cation (e) above, $R^2$ and $R^3$ are $C_1$-$C_6$ alkylene moieties; for example, difatty amido quats are commercially available from Witco under the Varisoft® tradename;

(f) $C_{8-22}$ quaternary surfactants such as isostearyl ethyl imidonium available in its ethosulfate salt form as Schercoquat IIS® from Scher Chemicals, Inc., quaternium-52 obtainable as Dehyquart SP® from Cognis Corporation, and dicoco dimethyl ammonium available in its chloride salt form as Arquad 2C-75® from Akzo Nobel Surface Chemistry LLC;

(g) Cationic esters such as discussed in U.S. Pat. No. 4,228,042, U.S. Pat. No. 4,239,660, U.S. Pat. No. 4,260,529 and U.S. Pat. No. 6,022,844;

(h) 4,5-dichloro-2-n-octyl-3-isothiazolone, which is obtainable as Kathon® from Rohm and Haas;

(i) Quaternary amino polyoxyalkylene derivatives (choline and choline derivatives);

(j) Alkyl oxyalkylene cations;

(k) Alkoxylate quaternary ammoniums (AQA) as discussed in U.S. Pat. No. 6,136,769;

(l) Substituted and unsubstituted pyrrolidinium, imidazolium, benzimidazolium, pyrazolium, benzpyrazolium, thiazolium, benzthiazolium, oxazolium, benzoxazolium, isoxazolium, isothiazolium, imdazolidenium, Guanidinium, indazolium, quinuclidinium, triazolium, isoquinuclidinium, piperidinium, morpholinium, pyridazinium, pyrazinium, triazinium, azepinium, diazepinium, pyridinium, piperidonium, pyrimidinium, thiophenium; phosphonium; in one embodiment, the cation is an substituted imidazolium cation having the formula:

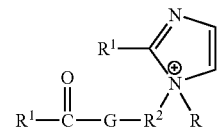

wherein each R and $R^1$ are as defined in cation (e) above; each $R^2$ is a $C_1$-$C_6$ alkylene group, preferably an ethylene group; and G is an oxygen atom or an —NR— group; for example, the cation 1-methyl-1-oleylamidoethyl-2-oleylimidazolinium is available commercially from the Witco Corporation under the trade name Varisoft® 3690; in another embodiment, the cation is alkylpyridinium cation having the formula:

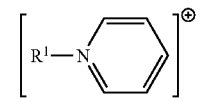

wherein $R^1$ is an acyclic aliphatic $C_8$-$C_{22}$ hydrocarbon group; in another embodiment, the cation is an alkanamide alkylene pyridinium cation having the formula:

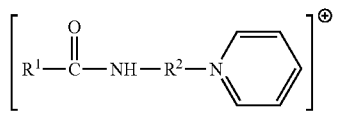

wherein $R^1$ is a linear or branched, saturated or unsaturated $C_6$-$C_{22}$ alkyl or alkoxy moiety, or a hydrocarbyl or substituted hydrocarbyl moiety, and $R^2$ is a $C_1$-$C_6$ alkylene moiety;

(m) Cationic bleach activators having a quaternary ammonium moiety including but not limited to

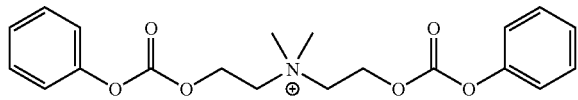

N,N-dimethyl-2-[(phenoxycarbonyl)oxy]-N-[2-[(phenoxycarbonyl)oxy]ethyl]ethanaminium

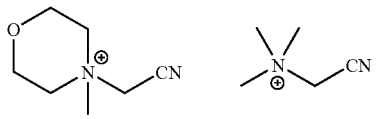

4-(cyanomethyl)-4-methylmorpholinium;
1-cyano-N,N,N-trimethylmethanaminium

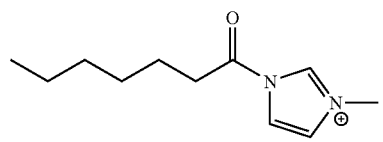

1-methyl-3-(1-oxoheptyl)-1H-Imidazolium these and other cationic bleach activators suitable for use herein as cations of the ionic liquids are disclosed in U.S. Pat. No. 5,599,781, U.S. Pat. No. 5,686,015, U.S. Pat. No. 5,686,015, WO 95/29160, U.S. Pat. No. 5,599,781, U.S. Pat. No. 5,534,179, EP 1 253 190 A1, U.S. Pat. No. 6,183,665, U.S. Pat. No. 5,106,528, U.S. Pat. No. 5,281, 361, and Bulletin de la Societe Chimique de France (1973), (3) (Pt. 2), 1021-7;

(n) Cationic anti-microbial agents, such as cetyl pyridinium, chlorohexidine and domiphen;

(o) Alkylated caffeine cations, such as

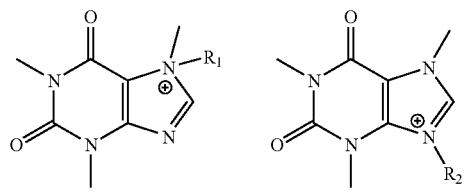

wherein $R_1$ and $R_2$ are C1 to C12 alkyl or alkylene groups; and (p) mixtures thereof.

The wide selection of cations provides the advantage of customizing the ionic liquids of the present invention for specific application or desired benefit. These cations can be selected and mixed with the surfactant derived anions described herein such that properties of the resulting ionic liquids can be customized. In some embodiments, the cations can be derived from known functional actives (e.g., cations derived from softeners) useful in consumer products such that, when paired with anions derived from surfactants, the resulting ionic liquids can provide the functional benefits that previously require multiple actives to achieve.

Ionic Liquids Applications

The ionic liquids of the present invention may be used in various consumer, institutional or industrial products, including but not limited to a laundry detergent, a dish cleaning detergent, a hard surface cleaning composition, a dry cleaning composition, an air care composition, a car care composition, a textile treating composition, or an industrial degreasing composition.

Without wishing to be bound by theory, it is believed that the fundamental chemical and/or physical properties on ionic liquids can be used advantageously in the surface or air treating compositions. In one aspect, ionic liquids have a high solubilizing ability, due to their high polarity and charge density; thus, ionic liquids can be an effective solvent for soils. Therefore, composition containing ionic liquids exhibit enhanced soil removal ability, compared to similar compositions without the ionic liquids. In another aspect, the functional groups and counterions of the ionic liquids can be varied such that the resulting ionic liquids are "tuned" to the characteristics of the target soil or surface. For example, the functional groups can be selected such that the resulting ionic liquids have the desired degree of hydrophilicity or hydrophobicity to interact more strongly or preferentially with the target soil or surface. The mechanisms by which ionic liquids can effectively interact with soil or substrates include, but are not limited to, charge transfer, ion exchange, van der Waals forces, and hydrogen bonding. In yet another aspect, the effective solvating property of the ionic liquids enables them to dissolve certain polymeric materials, which are soluble in few if any solvent media. Examples of such hard-to-dissolve polymers include, but are not limited to, biofilms, baked-on or cooked-on soils, polymerized soils, and the like.

In fabric cleaning and/or treating applications, ionic liquids provide high polarity without the detrimental effects of water. For example, water can cause damages to certain fabrics; the damage includes shrinkage, dye loss, shape loss, and wrinkles, etc.

Additionally, the nucleophilic and protic nature of water can lead to undesirable effects when formulating compositions intended for treating fabrics or similar soft surfaces. For example, water's ability to swell and hydrogen bond to cellulose can lead to increased abrasion and shrinkage of fabrics. Ionic Liquids can be tailored or selected to be non-nucleophilic and/or aprotic such that they would not have these adverse effects on cellulosic fibers or fabrics.

In still another aspect, the ionic liquids are non-volatile and nonflammable, and have high thermal stability; as such, they are especially suitable for use in surface or air treating compositions for both safety and aesthetic reasons. It is often undesirable to have chemical vapors or low flash points associated with compositions used in a consumer, industrial or institutional setting. It is also undesirable to have compositions that will leave unsightly streaks on surfaces treated by them. Commonly used organic cleaning solvents tend to have chemical vapors that may be toxic, flammable, or malodorous. Other commonly used compositions may leave unsightly or streaky residue on the treated surfaces, thus, they need to be removed (e.g., by wiping, rinsing, and the like) from the surfaces after application. In contrast, ionic liquids have essentially no vapor pressure (i.e., no detectable vapor pressure at or near room temperature); compositions using ionic liquids as the solvents or the active ingredients would avoid the problems associated with chemical vapors, thus, are highly advantageous. Additionally, such compositions can be used as a leave-on product and produce aesthetically pleasing results on the treated surfaces.

Thus, the unique and customizable physical and chemical properties allow ionic liquids to overcome several problems that persist in prior art compositions for treating soft or hard surfaces or air.

Accordingly, the present invention also relates to compositions, consumer products, and industrial products comprising the surfactant-derived ionic liquids, and the methods of using the same in following applications: dish/food cleaning, home care (kitchen/bath), biofilm removal, dry-cleaning (home & commercial), laundry (pretreatment, cleaning, and fabric care), textile processing & finishing, car care (interior and exterior), industrial degreasing, and air care.

The ionic liquid may be used in these applications or products as a pure solvent (i.e. as a pure, undiluted ionic liquid); as a co-solvent in conjunction with water or other organic solvents; or as an active where the continuous phase is water or another solvent (e.g. linear or cyclic siloxanes, halocarbons). Various adjunct ingredients known in the art may be incorporated into such compositions. In certain embodiments, water and/or solvent may be present in the composition at least about 0.01% or at least about 1% or at least about 10%, and less than about 90% or less than about 70% or less than about 50% by weight of the composition.

The ionic liquid compositions may be formulated in the form of liquid, gel, paste, foam, or solid. When the composition is in the solid form, it can be further processed into granules, powders, tablets, or bars.

The ionic liquid compositions may also comprise adjunct ingredients commonly used in air or surface treating compositions. When present, an adjunct ingredient may comprise from about 0.01 to about 10%, preferably from about 0.1 to about 5% by weight of the composition.

Suitable adjunct ingredients may be selected from the group consisting of enzymes, bleaches, surfactants, perfumes, co-solvents, cleaning agents, antibacterial agents, antistatic agents, brighteners, dye fixatives, dye abrasion inhibitors, anti-crocking agents, wrinkle reduction agents, wrinkle resistance agents, soil release polymers, sunscreen agents, anti-fade agents, particulate builders (e.g., silica, zeolites, phosphates), polymeric builders (e.g., polyacrylates, poly(acrylic-maeic) copolymers), sudsing agents, composition malodor control agents, dyes, colorants, speckles, pH buffers, waterproofing agents, soil repellency agents, and mixtures thereof.

Examples of suitable adjunct ingredients are disclosed in U.S. Pat. No. 6,488,943, Beerse et al.; U.S. Pat. No. 6,514, 932, Hubesch et al.; U.S. Pat. No. 6,548,470, Buzzaccarini et al.; U.S. Pat. No. 6,482,793, Gordon et al.; U.S. Pat. No. 5,545,350, Baker et al.; U.S. Pat. No. 6,083,899, Baker et al.; U.S. Pat. No. 6,156,722, Panandiker et al.; U.S. Pat. No. 6,573,234, Sivik et al.; U.S. Pat. No. 6,525,012, Price et al.; U.S. Pat. No. 6,551,986, Littig et al.; U.S. Pat. No. 6,566,323, Littig et al.; U.S. Pat. No. 6,090,767, Jackson et al.; and/or U.S. Pat. No. 6,420,326, Maile et al.

In some embodiments, such as laundry or dishwashing, ionic liquid compositions may be applied to the fabric or dish directly, or may be diluted with water to form a wash liquor, which contacts the fabric or dish. In other embodiments, the ionic liquid compositions may be in the form of a liquid, which can be applied to the target surface as a liquid spray, as an aerosol spray, or as a pour-on liquid, which can be poured onto the target surface directly or indirectly via a substrate such as a fibrous web substrate (made by woven, nonwoven or knitted technologies), a pulp-based substrate (made by air-felt or wet-laid technologies, including paper towels, tissues), a sponge, or a foam substrate. Another mode of use would be to incorporate ionic liquid compositions into or onto these substrates (e.g. impregnated in a wipe or a mitten), which would alleviate residue problems in those applications where complete dry down is needed.

The ionic liquid-containing compositions may be formulated in the form of liquid, gel, paste, foam, or solid. When the composition is in the solid form, it can be further processed into granules, powders, tablets, or bars. The composition may be employed as a component of another cleaning product, for example by application to an absorbent substrate to provide a wipe for use in various applications. Any suitable absorbent substrate may be employed, including woven or nonwoven fibrous webs and/or foam webs. It is preferred that such an absorbent substrate should have sufficient wet strength to hold an effective amount of the composition according to the present invention to facilitate cleaning. The ionic liquid-containing composition can also be included in unit dose products, which typically employ a composition of the present invention in a unit dose package comprising a water soluble polymer film. Exemplary unit dose package are disclosed in U.S. Pat. No. 4,973,416; U.S. Pat. No. 6,451,750; U.S. Pat. No. 6,448,212; and US 2003/0,054,966A1.

Preparation of Novel Surfactant Derived Ionic

Example 1

Preparation of Tetraoctyl Ammonium Mid-Chain Branched Dodecylsulfate Ionic Liquid To a solution of sodium mid-chain branched dodecylsulfate (5 g, 16.7 mmole) in 25 ml de-ionized water is added tetraoctylammonium bromide (9.1 g, 16.7 mmole) in 15 ml acetone. The mixture is stirred for 30 minutes at room temperature. After standing for 15 minutes in the reaction flask without stirring, the mixture separates into two layers by gravity. The upper organic layer is collected using a separatory funnel, and is subsequently dissolved in 25 ml methylene chloride. After standing for about 15 minutes, it separates into an aqueous layer and an organic layer The lower organic layer is collected using a separatory funnel, dried over anhydrous sodium sulfate for 5 minutes, filtered and concentrated on a rotary evaporator. The resultant oily material is stirred at 60 degrees C. and 0.1 mm Hg for 3 hours to remove last traces of solvent. This process produces a final product of about 10.2 g (about 84.1% yield) of viscous colorless oil comprising tetraoctyl ammonium mid-chain branched dodecylsulfate.

Example 2

Preparation of Triisooctylmethyl Ammonium Mid-Chain Branched Dodecylsulfate Ionic Liquid To a solution of sodium mid-chain branched dodecylsulfate (5 g, 16.7 mmole) in 25 ml de-ionized water is added trioctylmethyl ammonium chloride (6.7 g, 16.7 mmole) in 15 ml acetone. The mixture is stirred for 30 minutes at room temperature. After standing for 15 minutes in the reaction flask without stirring, the mixture separates into two layers by gravity. The upper organic layer is collected using a separatory funnel, and is subsequently dissolved in 25 ml methylene chloride. After standing for about 15 minutes, it separates into an aqueous layer and an organic layer The lower organic layer is collected using a separatory funnel, dried over anhydrous sodium sulfate for 5 minutes, filtered and concentrated on a rotary evaporator. The resultant oily material is stirred at 60 degrees C. and 0.1 mm Hg for 3 hours to remove last traces of solvent. This process produces a final product of about 7.7 g (about 76.3% yield) of viscous colorless oil comprising triisooctylmethyl ammonium mid-chain branched dodecylsulfate.

Example 3

Preparation of Tetraoctyl Ammonium Dodecylbenzenesulfonate

To a solution of sodium dodecylbenzenesulfonic acid (5 g, 80% active, tech grade, 11.5 mmole) in 25 ml de-ionized water is added tetraoctylammonium bromide (6.3 g, 11.5 mmole) in 15 ml acetone. After stirring 30 minutes at room temperature, the stirring is stopped and allowed to stand 15 minutes. The solution separates into two layers by gravity. The organic upper layer is collected in a separatory funnel. It is dissolved in 25 ml methylene chloride. After standing for 15 minutes, it separates into a small aqueous layer and an organic layer. The lower organic layer is collected using a separatory funnel, dried over anhydrous sodium sulfate for 5 minutes, filtered and concentrated on a rotary evaporator. The resultant oily material is stirred at 60 degrees C. and 0.1 mm Hg 18 hours to remove last traces of solvent. 8.5 g of viscous light brown oil resulted (94.2% yield).

Other surfactant-derived ionic liquids of the present invention can be made by these and similar processes.

Characterization of Ionic Liquids

The structures of the ionic liquids of the present invention are characterized by NMR (nuclear magnetic resonance). The melting temperatures of the ionic liquids are characterized by DSC (differential scanning calorimetry) from about 20° C. to about 100° C. at a scan rate of 10° C. per minute on heating cycles and 5° C. per minute on cooling cycles.

Water Miscibility Test

The water miscibility of an ionic liquid is measured by the following water miscibility test. A mixture of 0.5 g ionic liquid and 4.5 g de-ionized water are sonicated in a Bransonic Ultrasonic Bath (model # 1210R-MTH, 50/60 Hz, 117 volts, 1.3 AMPS) according to manufacture's specifications for 1.5 hours. Thereafter, if a homogenous transparent system results within 15 minutes of standing without agitation, then the ionic liquid is water miscible.

The nonlimiting examples of the surfactant-derived ionic liquids of the present invention shown below illustrate that the properties of the ionic liquids can be customized.

| Example | Anionic Surfactant | Cation | Liquid at Room Temp? | Melting Point Range | Water Miscible? |
|---|---|---|---|---|---|
| 1 | Mid-Chain Branched Dodecylsulfate | Tetraoctyl ammonium | Yes | 9.5 to −5.5 °C. | No |
| 2 | Mid-Chain Branched Dodecylsulfate | Triiosooctyl methyl ammonium | Yes | None detected by DSC | No |

-continued

| Example | Anionic Surfactant | Cation | Liquid at Room Temp? | Melting Point Range | Water Miscible? |
|---|---|---|---|---|---|
| 3 | Dodecylbenzene sulfonate | Tetraoctyl ammonium | Yes | not measured | No |

The following are nonlimiting examples of consumer product compositions containing ionic liquids of the present invention.

| | Composition Examples | | | | | |
|---|---|---|---|---|---|---|
| | 5 | 6 | 7 | 8 | 9 | 10 |
| Ionic Liquid 1[a] | — | 5 | — | 2 | — | — |
| Ionic Liquid 2[b] | 10 | — | — | — | 60 | — |
| Ionic Liquid 3[c] | — | — | 20 | — | — | 90 |
| Aesthetic Agents[1] | 1 | 1 | 1 | 1 | 1 | 1 |
| Enzymes[2] | 2 | — | — | 1 | — | — |
| Adjuncts[3] | 40 | 30 | 10 | 25 | 5 | 5 |
| Co-solvent[4] | — | 5 | 2 | — | 15 | 2 |
| Water | balance | balance | balance | balance | balance | balance |

[a]Tetraoctyl Ammonium Mid-chain Branched Dodecylsulfate.
[b]Triisooctylmethyl Ammonium Mid-chain Branched Dodecylsulfate.
[c]Tetraoctyl Ammonium Dodecylbenzenesulfonate.
[1]aesthetic agents may be selected from among the group consisting of dyes, colorants, speckles, perfumes and mixtures thereof.
[2]enzymes may be selected from among the group consisting of proteases, amylases, lipases, and mixtures thereof.
[3]adjuncts may be selected from among the group consisting of surfactants, enzymes, bleaching agents, preservatives and mixtures thereof.
[4]co-solvents may be selected from among the group consisting of ethanol, isopropanol, propylene glycol, and mixtures thereof All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An ionic liquid in the form of a liquid consisting of an amine oxide cation having the formula:

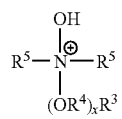

wherein $R^3$ is an $C_{8-22}$ alkyl, $C_{8-22}$ hydroxyalkyl, $C_{8-22}$ alkyl phenyl group, and mixtures thereof; $R^4$ is an $C_{2-3}$ alkylene or $C_{2-3}$ hydroxyalkylene group or mixtures thereof; x is from 0 to about 3; and each $R^5$ is an $C_{1-3}$ alkyl or $C_{1-3}$ hydroxyalkyl group or a polyethylene oxide group containing an average of from about 1 to about 3 ethylene oxide groups; or the $R^5$ groups are attached to each other, through an oxygen or nitrogen atom, to form a ring structure; and an anion selected from a group consisting of mid-chain branched alkyl sulfates, mid-chain branched alkyl aryl sulfonates and mid-chain branched alkyl polyoxyalkyene sulfates.

2. A method for treating a target surface comprising the step of:
contacting a target surface with an ionic liquid in the form of a liquid, wherein the ionic liquid consists of an amine oxide cation having the formula:

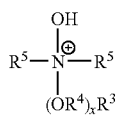

wherein $R^3$ is an $C_{8-22}$ alkyl, $C_{8-22}$ hydroxyalkyl, $C_{8-22}$ alkyl phenyl group, and mixtures thereof; $R^4$ is an $C_{2-3}$ alkylene or $C_{2-3}$ hydroxyalkylene group or mixtures thereof; x is from 0 to about 3; and each $R^5$ is an $C_{1-3}$ alkyl or $C_{1-3}$ hydroxyalkyl group or a polyethylene oxide group containing an average of from about 1 to about 3 ethylene oxide groups; or the $R^5$ groups are attached to each other, through an oxygen or nitrogen atom, to form a ring structure; and an anion selected from a group consisting of mid-chain branched alkyl sulfates, mid-chain branched alkyl aryl sulfonates and mid-chain branched alkyl polyoxyalkyene sulfates.

3. The method of claim 2 wherein the target surface is selected from a group consisting of soft surfaces, hard surfaces, and combinations thereof.

4. The method of claim 3 wherein the soft surfaces are selected from a group consisting of fabric articles, textiles, fibers, and combinations thereof; and the hard surfaces are selected from a group consisting of dishware, cookware, utensils, glassware, countertops, bathroom surfaces, kitchen surfaces, floors, windows, car interiors, car exteriors, metal and mixtures thereof.

5. An article of manufacture comprising a substrate and an ionic liquid in the form of a liquid associated with the substrate, wherein the ionic liquid consists of an amine oxide cation having the formula:

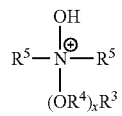

wherein $R^3$ is an $C_{8-22}$ alkyl, $C_{8-22}$ hydroxyalkyl, $C_{8-22}$ alkyl phenyl group, and mixtures thereof; $R^4$ is an $C_{2-3}$ alkylene or $C_{2-3}$ hydroxyalkylene group or mixtures thereof; x is from 0 to about 3; and each $R^5$ is an $C_{1-3}$ alkyl or $C_{1-3}$ hydroxyalkyl group or a polyethylene oxide group containing an average of from about 1 to about 3 ethylene oxide groups; or the $R^5$ groups are attached to each other, through an oxygen or nitrogen atom, to form a ring structure; and an anion selected from a group consisting of mid-chain branched alkyl sulfates, mid-chain branched alkyl aryl sulfonates and mid-chain branched alkyl polyoxyalkyene sulfates.

6. The article of manufacture of claim 5 wherein the substrate is selected from a group consisting of a woven fibrous substrate, a non-woven fibrous substrate, a knitted fibrous substrate, a pulp-based air-felt substrate, a pulp-based wetlaid substrate, a foam, a sponge, and combinations thereof.

* * * * *

UNITED STATES PATENT AND TRADEMARK OFFICE
CERTIFICATE OF CORRECTION

| | | |
|---|---|---|
| PATENT NO. | : 7,786,064 B1 | Page 1 of 1 |
| APPLICATION NO. | : 12/771588 | |
| DATED | : August 31, 2010 | |
| INVENTOR(S) | : Hecht et al. | |

It is certified that error appears in the above-identified patent and that said Letters Patent is hereby corrected as shown below:

Column 2
Line 43, delete "minors" and insert --mirrors--.

Signed and Sealed this
Twenty-eighth Day of June, 2011

David J. Kappos
*Director of the United States Patent and Trademark Office*